United States Patent [19]
Yankielun

[11] Patent Number: 6,084,393
[45] Date of Patent: Jul. 4, 2000

[54] SCOUR PROBE ASSEMBLY

[75] Inventor: Norbert Edward Yankielun, Lebonon, N.H.

[73] Assignee: U.S. Army Corps of Engineers as represented by the Secretary of the Army, Washington, D.C.

[21] Appl. No.: 09/418,483

[22] Filed: Oct. 15, 1999

[51] Int. Cl.[7] .............................. G01N 27/00; G01N 3/08; G01N 3/00; G01N 27/02

[52] U.S. Cl. .................. 324/72.5; 324/326; 324/334; 324/345; 324/449; 340/870.33

[58] Field of Search .................... 324/72.5, 326, 324/334, 345, 344, 335, 207.22, 449; 340/870.33

[56] References Cited

U.S. PATENT DOCUMENTS

| | | | |
|---|---|---|---|
| 4,269,397 | 5/1981 | Strimple et al. | 266/44 |
| 4,742,305 | 5/1988 | Stolarczyk | 324/334 |
| 4,914,394 | 4/1990 | Meyer | 324/534 |
| 5,435,170 | 7/1995 | Voelker et al. | 324/449 |
| 5,532,687 | 7/1996 | Richardson et al. | 340/870.33 |
| 5,554,936 | 9/1996 | Mohr | 324/642 |
| 5,784,338 | 7/1998 | Yankielun | 367/131 |
| 5,790,471 | 8/1998 | Yankielun | 367/13 |
| 5,923,170 | 7/1999 | Kuckes | 324/326 |

*Primary Examiner*—Glenn W. Brown
*Assistant Examiner*—James C. Kerveros
*Attorney, Agent, or Firm*—Luther A. Marsh

[57] ABSTRACT

A scour probe assembly comprises an elongated rigid tubular member of electrically insulative material, an anchoring structure fixed to a distal end of the tubular member, and a signal transmission device mounted on the tubular member. A pair of substantially parallel electrically conductive sensor lines are fixed to an external wall of the tubular member and extend along at least a portion of an axial length of the tubular member from a closed proximal end toward the distal end and extend through the closed proximal end to an interior of the tubular member. Electronic components are disposed in the interior of the tubular member and are interposed between ends of the sensor lines in the interior of the tubular member and the signal transmission device mounted in the tubular member.

12 Claims, 7 Drawing Sheets

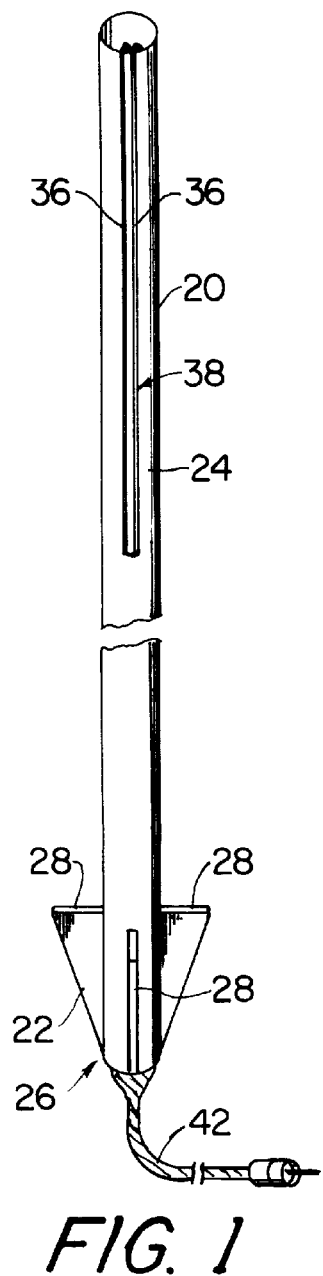
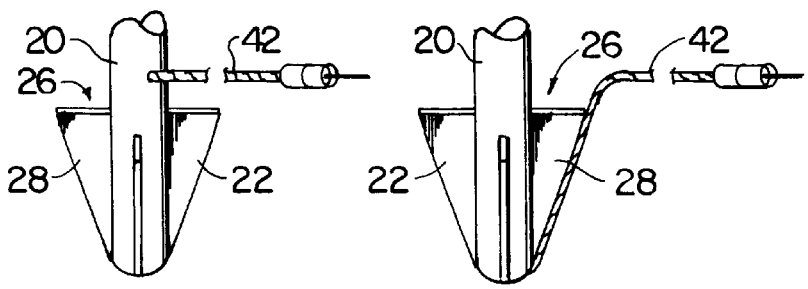
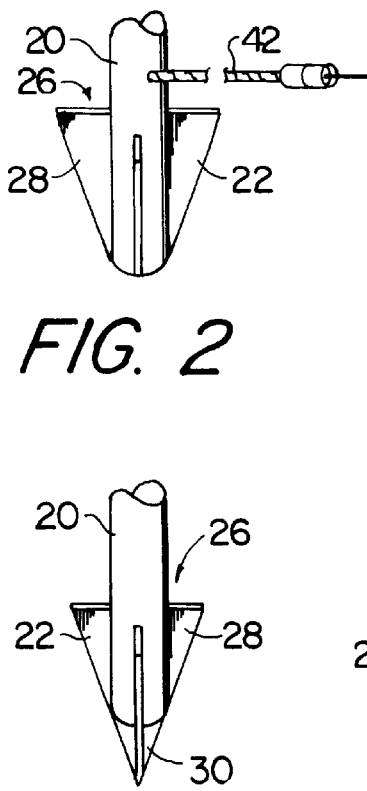
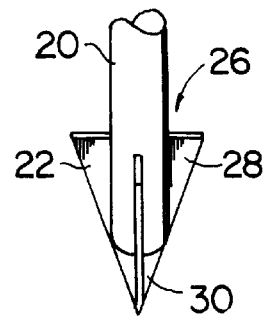
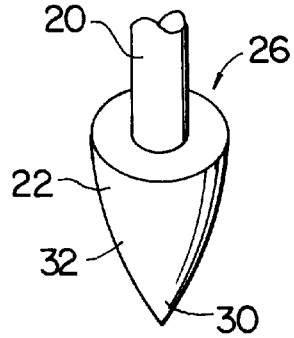
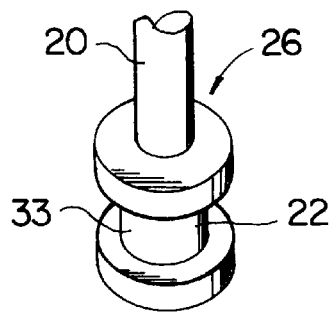

SCOUR PROBE ASSEMBLY

BACKGROUND OF THE INVENTION

1. Field of the Invention

The invention relates to detection and monitoring devices and is directed more particularly to an assembly for detecting and monitoring the presence of scour in underwater beds, such as river beds, navigational channels, and the like.

2. Description of the Prior Art

Scour is a severe problem that results in millions of dollars of damage to infrastructure and substantial loss of life annually. Scour occurs during times of high tides, hurricanes, rapid river flow, and icing conditions when sediment, including rocks, gravel, sand, and silt, are transported by currents, undermining bridge pier foundations, submarine utility cables and pipelines, and filling in navigational channels. Scour is dynamic; ablation and deposition can occur during the same high energy hydrodynamic event. The net effect cannot be easily predicted nor readily monitored in real-time.

Bridge scour monitoring technologies are known. In U.S. Pat. No. 5,784,338, issued Jul. 21, 1998 to Norbert E. Yankielun et al, an instrument called a "time domain reflectomer" (TDR) is directly connected to a parallel transmission line consisting of a pair of robust, specially fabricated non-corroding rods or wires. The principle of TDR is known, described in the technical literature, and applied to numerous measurement and testing applications. This technique was applied to scour detection and monitoring in the '338 patent, which is incorporated herein by reference. TDR operates by generating an electromagnetic pulse, or a fast rise time step, and coupling it to a transmission line. The pulse propagates down the transmission line at a fixed and calculable velocity, a function of the speed of light and the electrical and physical characteristics of the transmission line. The pulse propagates down the transmission line until the end of the line is reached, and is then reflected back toward the source. The time in seconds that it takes for the pulse to propagate down and back the length of the transmission line is called the "round trip travel time" and is calculated as described in the '338 patent.

For a two wire parallel transmission line, changes in the dielectric media in the immediate surrounding volume causes a change in the round trip travel time. Freshwater has a relatively high dielectric constant and dry sedimentary materials (e.g.: soil, gravel and stone) have a relatively low dielectric constant. Wet sediment has a dielectric constant that is a mixture of those of water and dry soil. The dielectric constant of this mixture will vary depending upon the local sedimentary material constituency, but in all cases of bulk dielectric (bulk index of refraction) of the mixture will be less than that of liquid water alone and significantly greater than that of the dry sedimentary materials. Some sediment materials, particularly clay-based sediments, can be extremely "lossy". This lossy behavior of the soil is exhibited by a severe attenuation of an electromagnetic pulse as it propagates along a transmission line surrounded by such materials. The pulse, when launched from a TDR will dissipate as it travels along the transmission line. Sufficient dissipation will reduce the reflected pulse energy below a detectable level.

At any boundary condition along the transmission line (e.g., air/water and water/sediment), a dielectric discontinuity exists. As a pulse traveling down the transmission line from the TDR source encounters these boundary conditions, a portion of pulse energy is reflected back to the source from the boundary. A portion of the energy continues to propagate through the boundary until another boundary or the end of the cable causes all or part of the remaining pulse energy to return along the transmission line toward the source. Measuring the time of flight of the pulse and knowing the dielectric medium through which the pulse is traveling permits calculation of the physical distance from the TDR source of each of the dielectric interface boundaries encountered.

For lossy consolidated soils, such as clay, the electromagnetic signal is greatly attenuated as it propagates along the imbedded transmission line. Levels of signal attenuation can be as much as 10's of decibels per meter. This results in little or no reflected signal returned to the instrument over the length of the probe buried in the lossy media. If the sensor source is imbedded in lossy media along with a portion of the sensor probe, the media will absorb (dissipate) all the pulse energy. Little or no reflected signal is returned. If a pulse is propagating along a transmission line imbedded in a non- or minimally-lossy material and a boundary with some extremely lossy material is encountered, a reflection will occur at the interface boundary, similarly to that that would occur for a boundary between two non-lossy materials. The magnitude of the reflection will be proportional to the reflection coefficient of the two materials at the interface.

In U.S. Pat. No. 5,790,471, issued Aug. 4, 1998 to Norbert E. Yankielun et al, there is disclosed a Water/Sediment Interface Monitoring System Using a Frequency-Modulated Continuous Wave reflectometer. The frequency modulated continuous wave (FM-CW) technique is known with respect to radar systems. In this system, instead of launching electromagnetic waves from an antenna into free space, as would be done in a radar application, the waves are coupled to a transmission line, such as a parallel line sensor or the like, as described above.

In an FM-CW reflectometer system, a steady amplitude signal whose frequency increases linearly with time is transmitted down a transmission line. The FM-CW signal is produced by a voltage controlled oscillator (VCO) driven by a linear ramp generator. This signal, coupled to the transmission line, propagates down the line and is reflected from the far end, or intermediate discontinuity, returning to the source, delayed by the round-trip propagation time, all as described in the '471 patent which is incorporated herein by reference.

This signal can be directly processed, analyzed, and stored or displayed. Alternatively, this signal can be transmitted to a remote location over twisted pair, coaxial cable, radio, or other form of telemetry, where it then can be processed, analyzed, etc.

Lossy sediments cause the same signal dissipation effect with the FM-CW reflectometer as experienced with the TDR. These instruments have proved successful in detecting, monitoring and measuring scour and deposition of sediments in freshwater. Existing implementations use a transmission sensor consisting of two parallel rods. This two-pronged unit is physically large and robust, and can survive deployment in high current rivers. This implementation, while successful at measuring sedimentation and scour, has a large cross-section, and therefore a tendency to more easily snag submerged current-borne debris. The implementation disclosed here employs a single, robust, vertical cylinder with sensor transmission line wires (or conductive tapes) bonded vertically along the outside axial length of the cylinder. The entire unit is watertight and corrosion-resistant. The cylinder houses the scour probe electronics and other associated hardware. This probe is suitable for use in both high current and low flow in freshwater applications and will operate in low-loss or lossy sediments.

There is a need for a probe for detecting and monitoring scour, which probe is structured to accept either TDR of FM-CW reflectometer packages and which is provided with a limited profile, or cross-section so as to reduce collision with water-borne debris.

SUMMARY OF THE INVENTION

An object of the invention is, therefore, to provide a scour probe assembly adapted to house a selected one of a TDR and FM-CW reflectometer and to provide for interconnection of the selected reflectometer and a pair of sensor lines, and the reflectometer and a selected signal transmission means.

A further object of the invention is to provide such an assembly as is relatively small in cross-section and shaped to minimize collisions with water-borne debris.

With the above and other objects in view, as will hereinafter appear, a feature of the present invention is the provision of a scour probe assembly comprising an elongated rigid tubular member of electrically insulative material, an anchoring structure fixed to a distal end of the tubular member, and a signal transmission means mounted on the tubular member. A pair of substantially parallel electrically conductive sensor lines are fixed to an external wall of the tubular member and extend along at least a portion of an axial length of the tubular member from a closed proximal end toward the distal end. The lines extend through the closed proximal end to an interior of the tubular member. Electronic components are disposed in the interior of the tubular member and are interposed between ends of the sensor lines in the interior of the tubular member and the signal transmission means mounted in the tubular member.

In accordance with a further feature of the invention, the electronic components disposed in the interior of the tubular member comprise a selected one of a time domain reflectometer and a frequency modulated-continuous wave reflectometer.

In accordance with a further feature of the invention, the aforesaid tubular member is only 2–4 inches in diameter.

In accordance with a still further feature of the invention, there is provided a scour probe assembly comprising an elongated rigid tubular member of electrically insulative material, an anchoring structure fixed to a distal end of the tubular member, and a signal transmission cable mounted on the tubular member. A pair of substantially parallel electrically conductive sensor lines are fixed to an external wall of the tubular member and extend along at least a portion of an axial length of the tubular member from a closed proximal end toward the distal end. The lines extend through the closed proximal end to an interior of the tubular member, and are in communication with a first end of the signal transmission cable. The signal transmission cable is provided with a second end adapted to be placed in communication with a reflectometer remote from the tubular member.

The above and other features of the invention, including various novel details of construction and combinations of parts, will now be more particularly described with reference to the accompanying drawings and pointed out in the claims. It will be understood that the particular devices embodying the invention are shown by way of illustration only and not as limitations of the invention. The principles and features of this invention may be employed in various and numerous embodiments without departing from the scope of the invention.

BRIEF DESCRIPTION OF THE DRAWINGS

Reference is made to the accompanying drawings in which are shown illustrative embodiments of the invention, from which its novel features and advantages will be apparent.

In the drawings:

FIG. 1 is a perspective view of one form of scour probe assembly illustrative of an embodiment of the invention;

FIGS. 2–6 illustrate alternative embodiments of portions of the illustrative scour probe assembly;

DESCRIPTION OF THE PREFERRED EMBODIMENT

Figure 7:
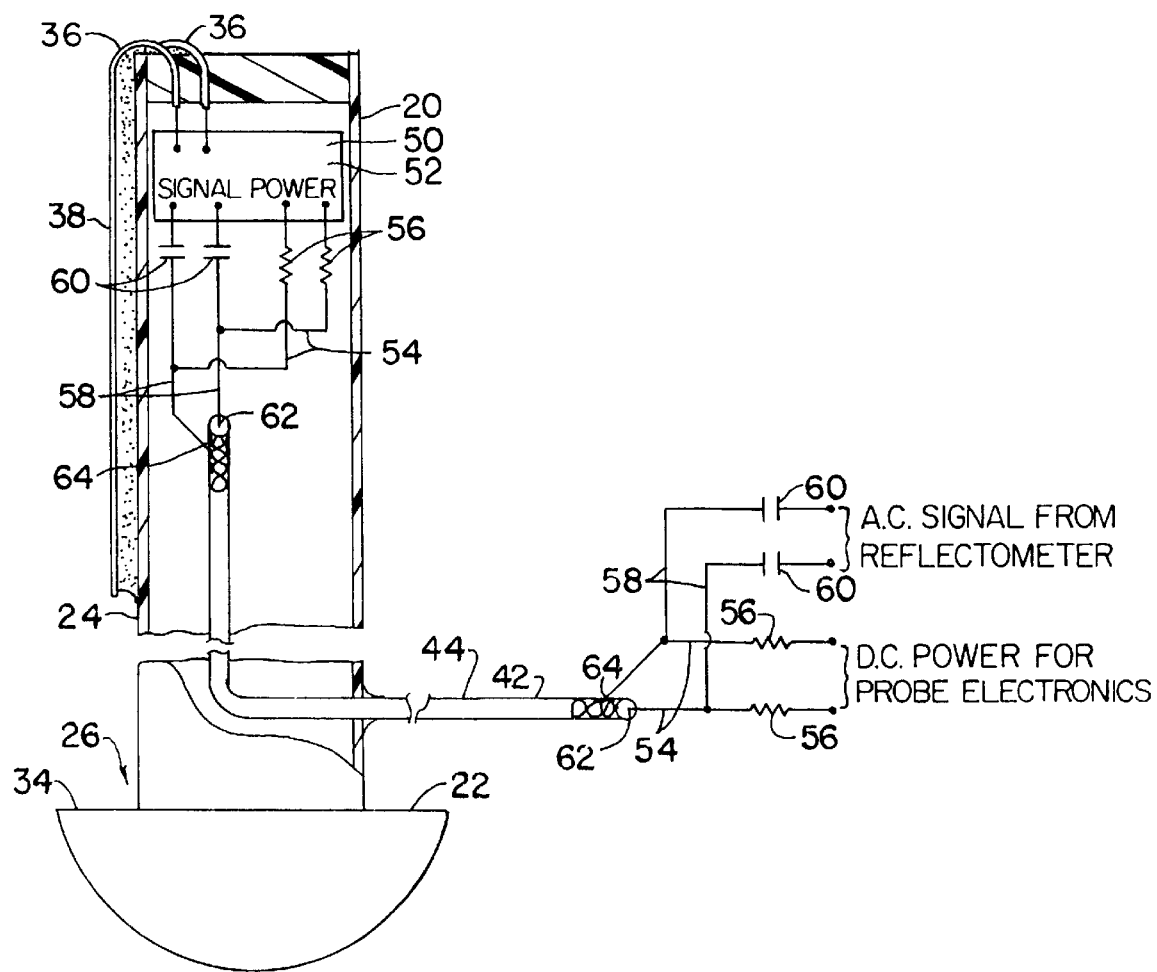
FIGS. 7 is a partly sectional and partly perspective diagrammatical illustration of a scour probe assembly similar to that shown in FIG. 1.

Referring to FIG. 1 it will be seen that an illustrative embodiment of the scour probe assembly includes an elongated rigid tubular member 20 of a non-electrically-conductive insulating material, such as PVC of fiberglass. The width-wise cross-section of the tube 20 may be circular, hydrofoil-like, triangular, or quadrilaterally shaped. While the hydrofoil or polygonal configurations have hydrodynamic advantages in some applications, the ready availability of circular tubing renders it a preferred choice in most instances. Typically, the tubular member is 6–10 feet in length and 2–4 inches in outside diameter, with a wall thickness of about ⅛ inch to ¼ inch.

An anchoring structure 22 is fixed to a distal end 26 of the tubular member 20. The anchoring structure comprises one or more weighted members, such as flukes 28 extending radially outwardly from the tubular member 20 (FIGS. 1–4). The flukes 28 may extend beyond the distal end of the tubular member 20 to form a point 30 (FIG. 4). Alternatively, the anchoring structure may comprise a generally frusto-conically shaped body 32 (FIG. 5) which brings to bear more weight than the flukes 28 and may be provided with the point 30. Another embodiment of the anchoring structure 22 comprises a spool-shaped body 33 (FIG. 6) which is particularly suitable for back-fill installations. In FIGS. 7–11 there is illustrated still another useful embodiment of anchoring structure, namely a bulbous bottom-rounded heavy weight 34 which by virtue of its weight exercises strong holding power, but by virtue of its rounded bottom permits a degree of rocking movement to absorb a collision or extremely strong forces in the water, as might be caused by natural forces or an underwater explosion, or the like.

Figure 12:
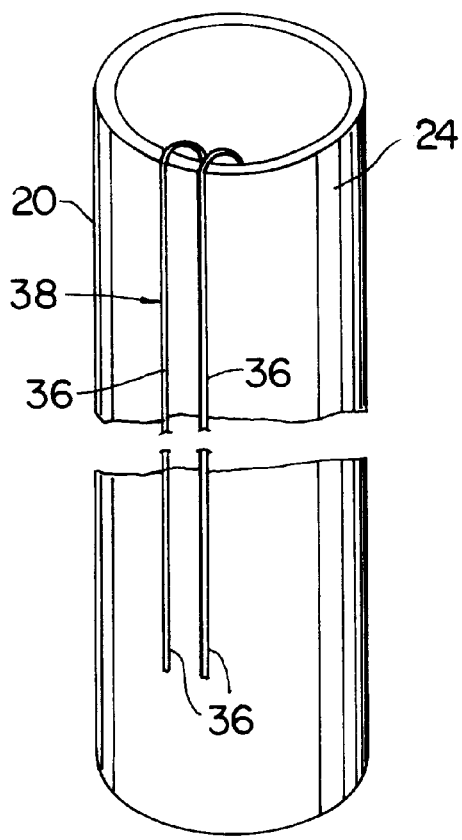
FIGS. 12 and 13 are perspective views of alternative arrangements of sensor portions of the scour probe assembly.
Figure 13:
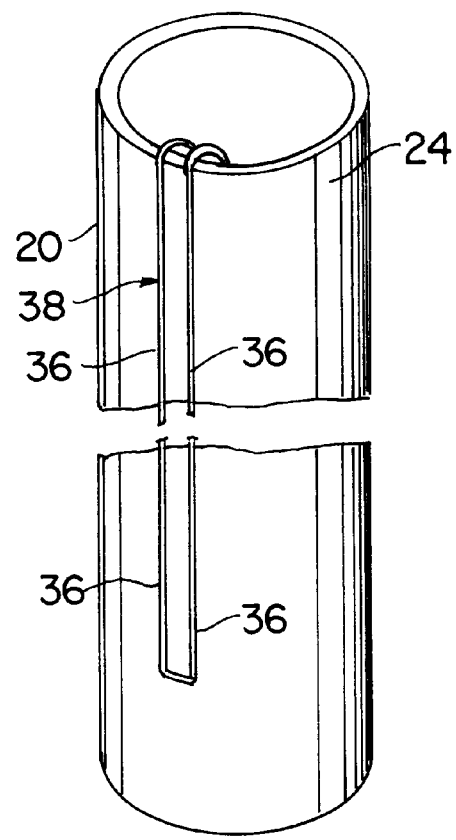

The assembly further includes a pair of substantially parallel electrically conductive leads 36 forming a reflectometer sensor 38 (FIGS. 1 and 7–11). The leads 36 may comprise wires or rods and typically are about 3–6 feet long, depending upon the length of the tubular member 20. The leads 36 are fixed to and extend along the outside wall of the tubular member 20, from a closed proximal end 40 thereof toward the distal end. The diameter and spacing of the leads preferably are determined so as to ensure an impedance match between the leads 36 and surrounding sediments. The diameter of the leads usually is about 1/16 to 1/8 inch. The sensor 38 can be fabricated by affixing two separate parallel sensor lines 36 to the exterior wall 24 of the tubular member 20, or, for applications not requiring a robust assembly, by affixing a length of parallel transmission line ("twin lead") to the tubular member. The two lines 36 may be short-circuited (FIG. 13) or open circuited (FIG. 12) at the lower extremity thereof. An open or short circuit does not substantially affect the operation of the probe, except to determine the polarity of the reflected pulse. An open-circuited pair of sensor lines reflect the pulse with the same polarity as transmitted. A short-circuited pair of sensor lines reflect the pulse with the opposite polarity from that transmitted. The two lines 36 extend from the interior of the tubular member 20, through the closed proximal end 40 and along at least a portion of the axial length of the tubular member.

The scour probe assembly still further includes a signal transmission means 42 for transmitting signals from the probe assembly to a remote station (not shown). The signal transmission means 42 may comprise an umbilical coaxial cable 44 in hardwire communication with the remote station, or an antenna 46 including a whip portion 48, shown in FIGS. 9 and 10, or a helical or loop portion (not shown) wound around the top of the tubular member 20, for wireless communication with the remote station.

The scour probe assembly still further includes an electronic component package 50 disposed in the tubular member 20 and interposed between ends of the sensor lines 36 in the tubular member 20 and the signal transmission means 42 mounted in the tubular member.

In the embodiment illustrated in FIG. 7, the electronic components package 50 comprises a time domain reflectometer (TDR) 52 disposed between the reflectometer sensor 38 and the coaxial cable 44, and of the type discussed in detail in the aforementioned '338 patent. The cable 44 provides DC power for the probe electronics through lines 54 having therein AC blocking inductors 56. The cable 44 further facilitates transmission of AC signals from the TDR reflectometer 52 through lines 58 having therein DC blocking capacitors 60, as is shown schematically in FIG. 7. The lines 54, 58 lead from the cable center conductor 62 and coax shield 64, respectively, as illustrated.

Figure 14:
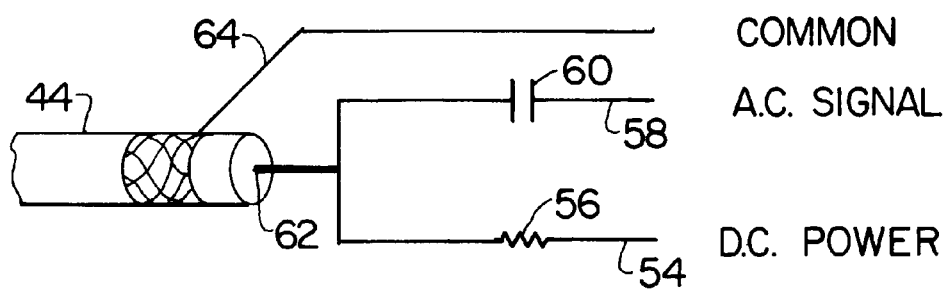
FIG. 14 is a schematic illustration of an alternative electrical connection assembly for the scour probe assembly.

It will be apparent that other electrical connectors at the ends of the coaxial cable 44 may be utilized. An alternative arrangement for both ends of the cable 44 is shown in FIG. 14 wherein a common line 66 is taken from the shield 64 and both the DC power line 54 and AC signal lines 58 are taken off the cable center conductor 62. The AC signal line 58 is provided with a DC blocking capacitor 60 and the DC power line 54 is provided with an AC blocking inductor 56.

Figure 8:
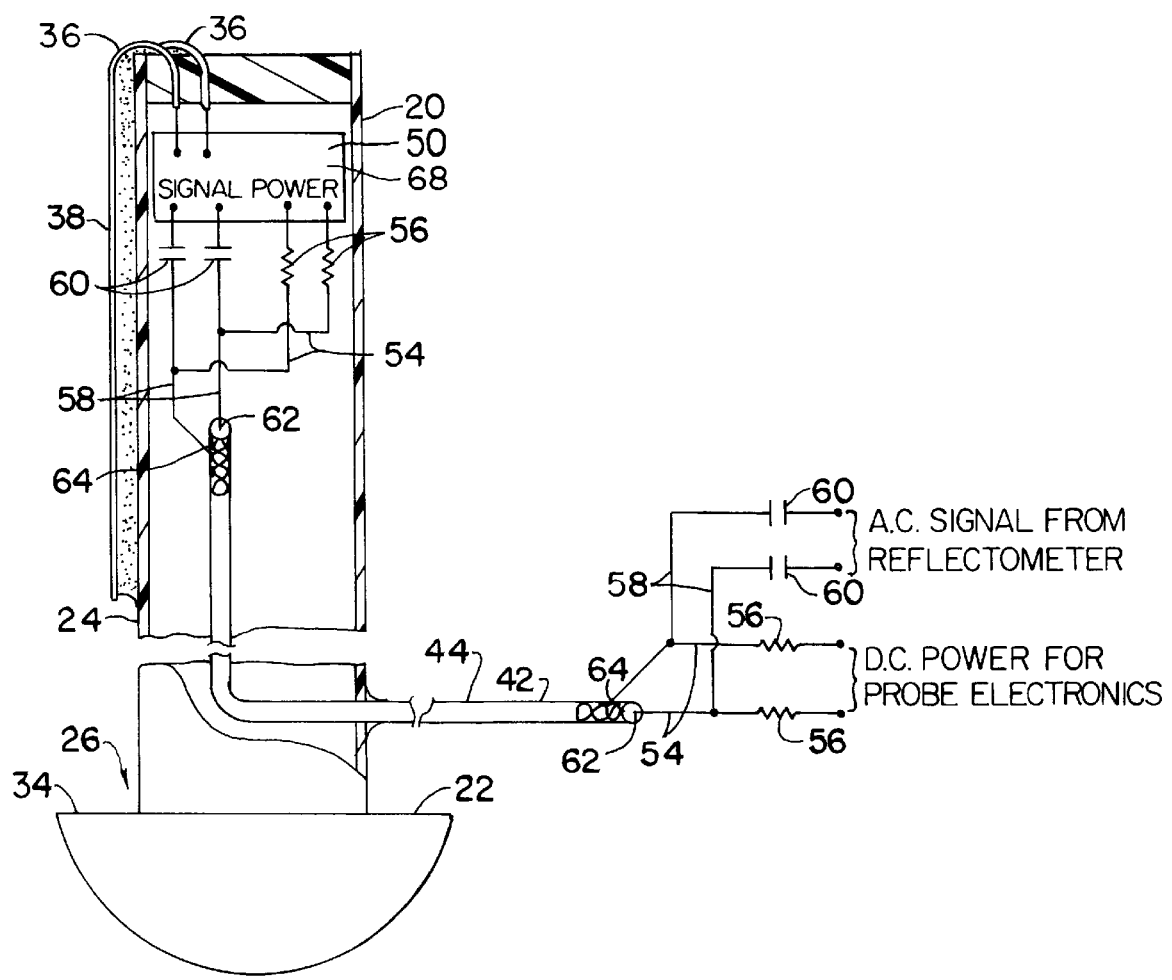
FIG. 8 is similar to FIG. 7, but showing an alternative embodiment.

In the embodiment illustrated in FIG. 8, the electronic components package 50 comprises a frequency modulated-continuous wave (FM-CW) reflectometer 68 disposed between, and connected to, the sensor 38 and cable 44 similarly to the TDR 52 of FIG. 7.

Figure 9:
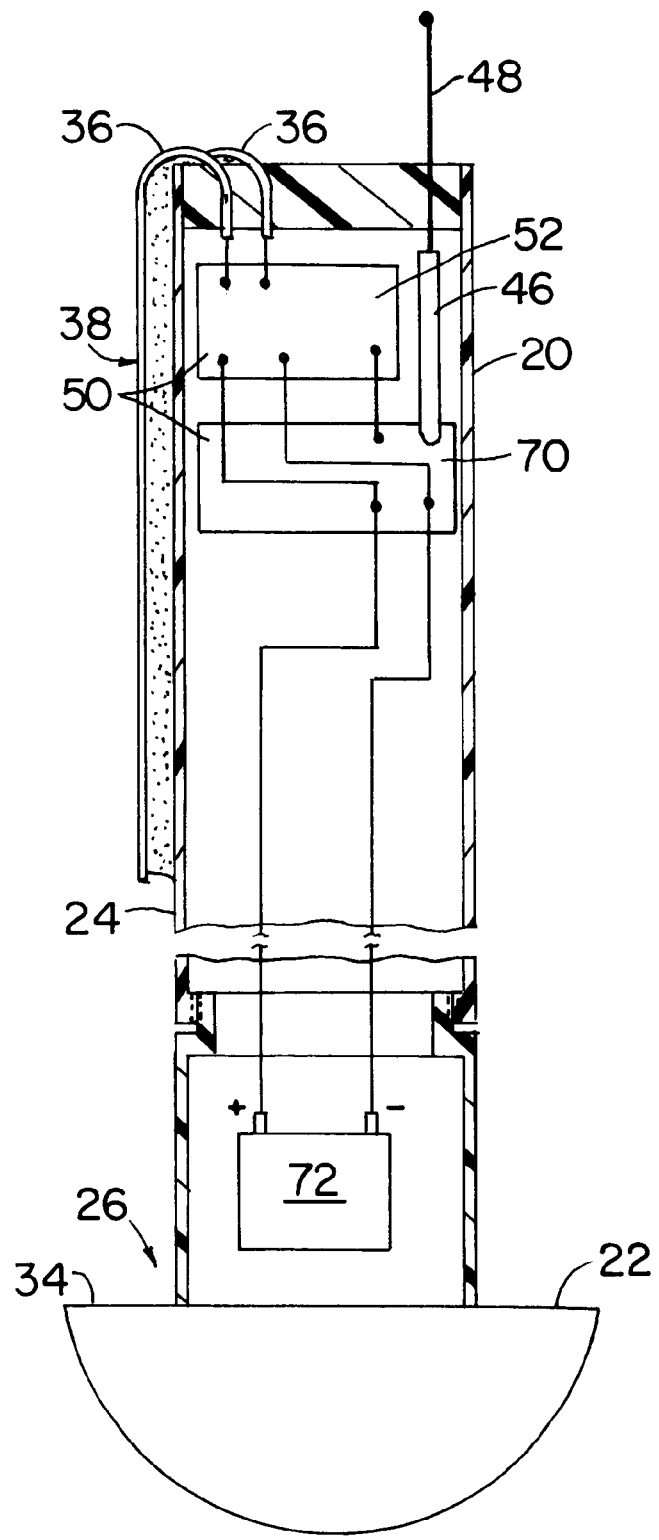
FIGS. 9 and 10 are similar to FIG. 7, but show further alternative embodiments.

In the embodiment illustrated in FIG. 9, the electronic components package 50 comprises the TDR 52 and a VHF or UHF telemetry transmitter 70. The signal transmission means 42 comprises the antenna 46 connected to the telemetry transmitter 70. A battery 72 provides DC power to the transmitter 70 and the TDR 52.

Figure 10:
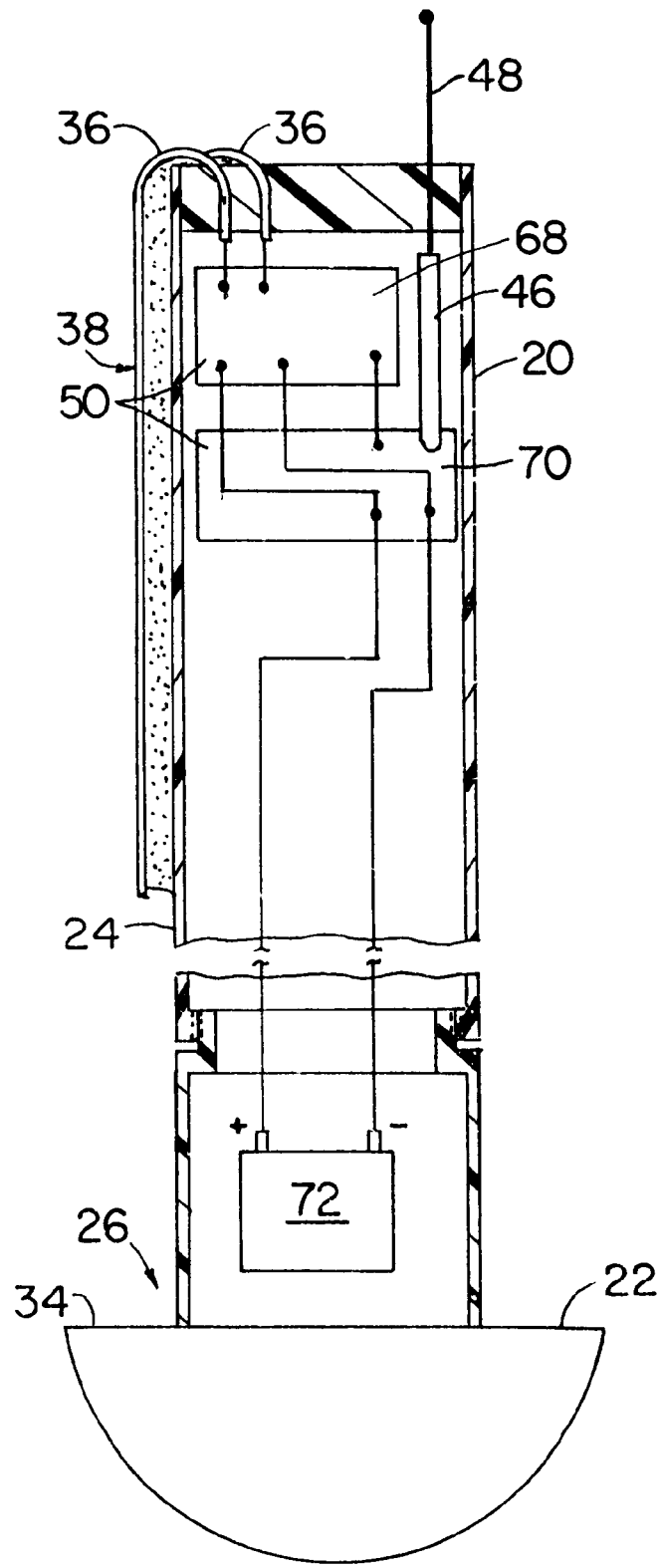

In the embodiment illustrated in FIG. 10, the electronic components package 50 comprises the FM-CW reflectometer 68 and the telemetry transmitter 70. The probe of FIG. 10 is similar to the probe of FIG. 9 except that the reflectometer is an FM-CW reflectometer, rather than a TDR.

Thus, in the embodiments of FIGS. 9 and 10, the tubular member 20 houses the reflectometer electronic 50, either TDR 52 or FM-CW reflectometer 68, a VHF or UHF telemetry transmitter 70, and the battery 72 to power the unit for a year, or so. The tubular member 20 of the embodiments of FIGS. 9 and 10 is provided with a water-tight thread connection 74 between lower and upper portions of the tubular member to permit replacement of the battery 72.

The cable-based embodiments of FIGS. 7 and 8 are suitable for long-term or permanent monitoring situations. The telemetry based embodiments of FIGS. 9 and 10 are appropriate for shorter term applications wherein the probe can be retrieved for refurbishing and replacement of batteries.

Figure 11:
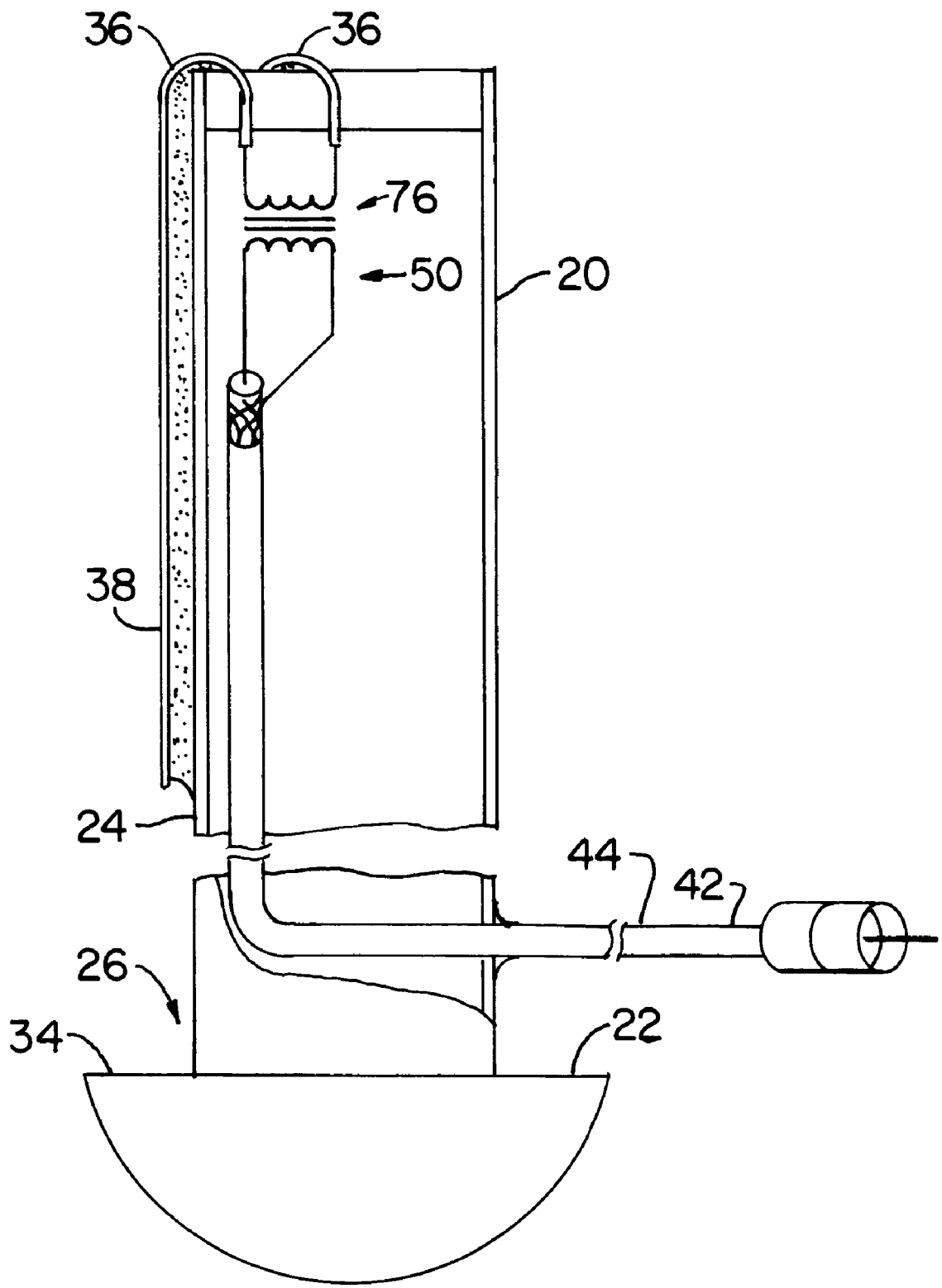
FIG. 11 is similar to FIGS. 7–10, but shows a still further embodiment of scour probe assembly.

In FIG. 11 there is shown an alternative embodiment in which the reflectometer sensor leads 36 are connected to the coaxial cable 44 in the tubular member 20, and the cable 44 is in communication with a TDR or FM-CW reflectometer at a location remote from the probe assembly, as in an ashore monitoring station. In this embodiment, there may be no electronic package between the sensor 38 and the cable 44, or the electronic package 50 may comprise merely an impedance matching transformer 76.

In all of the embodiments described hereinabove, the tubular member 20 may be filled with a potting compound, embedding the internal components, to increase the strength of the assembly and to improve water cooling of the internal components.

In installation, the scour probe assembly is buried in river bottom sediments and anchored at a point below the maximum expected depth of scour. Primarily, the probe is designed for installation by "air jetting". Alternatively, the probe can be installed in softer sediments by being "pile driven" or hydraulically forced into the sediments. The top of the probe is "surveyed in" relative to a local survey benchmark.

Following installation, an initial reference reading is made of the probe signal response, and the round trip travel time for a pulse propagating along each transmission line sensor is calculated and stored in an associated computer (not shown). Subsequent probe signal responses and round-trip propagation times are frequently and automatically (or manually) acquired, calculated, and compared with the original reference data set. A real-time computer algorithm can be used to compare the reference round-trip travel time with subsequent values, trigger an alarm when a significant change is observed in the probe signal response or a threshold difference in round trip travel time is reached. Depending on the desired implementation, an automatic electronic multiplexer can be arranged with the instrument to monitor a sensor array consisting of numerous probes installed in close proximity to a structure of interest.

There is thus provided a probe for detecting and monitoring scour. The probe is structured to accept either TDR or FM-CW reflectometer electronics. The probe is further of very thin cross-section so as to reduce collisions with underwater moving objects.

It will be understood that many additional changes in the details, materials, steps and arrangement of parts, which have been herein described and illustrated in order to explain the nature of the invention, may be made by those skilled in the art within the principles and scope of the invention as expressed in the appended claims.

What is claimed is:

1. A scour probe assembly comprising:
an elongated rigid tubular member of electrically insulative material;
an anchoring structure fixed to a distal end of said tubular member;
signal transmission means mounted on said tubular member;
a pair of substantially parallel electrically conductive sensor lines fixed to an external wall of said tubular member and extending along at least a portion of an axial length of said tubular member from a closed proximal end toward said distal end and extending through said closed proximal end to an interior of said tubular member; and
electronic components disposed in the interior of said tubular member and interposed between ends of said sensor lines in the interior of said tubular member and said signal transmission means mounted in said tubular member.

2. The assembly in accordance with claim 1 wherein said anchoring structure comprises a selected one of a group of anchoring structures, the group consisting of flukes extending radially outwardly from said tubular member, flukes extending radially outwardly and distally from said tubular member, a body having a distal point thereon, a body having a distal blunt surface thereon, and a body having a distal rounded surface thereon.

3. The assembly in accordance with claim 1 wherein said signal transmission means comprises a cable fixed at a first end to said assembly, and at a second end adapted for connection to a remote monitoring station.

4. The assembly in accordance with claim 3 wherein said cable enters said tubular member at a selected one of said distal end of said tubular member, proximate but removed from said distal end of said tubular member, and through said anchoring structure.

5. The assembly in accordance with claim 3 wherein said electronic components comprise a reflectometer in communication with said sensor lines, and in communication with said cable.

6. The assembly in accordance with claim 5 wherein said reflectometer comprises a selected one of a time domain reflectometer and a frequency modulated-continuous wave reflectometer.

7. The assembly in accordance with claim 1 wherein said signal transmission means comprises an antenna fixed to and extending from said assembly.

8. The assembly in accordance with claim 7 wherein said electronic components comprise a reflectometer in communication with said sensor lines, and a telemetry transmitter in communication with said reflectometer and said antenna.

9. The assembly in accordance with claim 8 wherein said reflectometer comprises a selected one of a time domain reflectometer and a frequency modulated continuous wave reflectometer.

10. The assembly in accordance with claim 8 and further comprising a battery disposed in said tubular member for providing power to said transmitter and said reflectometer.

11. A scour probe assembly comprising:
an elongated rigid tubular member of electrically insulative material;
an anchoring structure fixed to a distal end of said tubular member;
a signal transmission cable mounted on said tubular member;
and
a pair of substantially parallel electrically conductive sensor lines fixed to an external wall of said tubular member and extending along at least a portion of an axial length of said tubular member from a closed proximal end toward said distal end, and extending through said closed proximal end to an interior of said tubular member, and in communication with a first end of said signal transmission cable;
said signal transmission cable having a second end adapted to be placed in communication with a reflectometer remote from said tubular member.

12. The assembly in accordance with claim 11 and further comprising an impedance matching transformer interposed between said sensor lines in the interior of said tubular member, and a portion of said signal transmission cable disposed in said tubular member.

* * * * *